United States Patent [19]
Pettit et al.

[11] Patent Number: 5,410,024
[45] Date of Patent: Apr. 25, 1995

[54] HUMAN CANCER INHIBITORY PENTAPEPTIDE AMIDES

[75] Inventors: George R. Pettit, Paradise Valley, Ariz.; Jozsef Barkoczy, Budapest, Hungary; Darko Kantoci, Tempe, Ariz.

[73] Assignee: Arizona Board of Regents acting on behalf of Arizona State University, Tempe, Ariz.

[21] Appl. No.: 6,465

[22] Filed: Jan. 21, 1993

[51] Int. Cl.$^6$ .......................... C07K 7/00; C07K 7/06; A61K 38/00
[52] U.S. Cl. .................................................. 530/330
[58] Field of Search .......................... 530/330; 514/17

[56] References Cited

U.S. PATENT DOCUMENTS

| | | | |
|---|---|---|---|
| 4,486,414 | 12/1984 | Pettit | 514/2 |
| 4,879,278 | 11/1989 | Pettit et al. | 530/330 |
| 4,978,744 | 12/1990 | Pettit et al. | 530/330 |
| 5,076,973 | 12/1991 | Pettit et al. | 530/317 |
| 5,138,036 | 8/1992 | Pettit et al. | 530/317 |

OTHER PUBLICATIONS

Dermer, Biotechnology, vol. 12, Mar. 1994.

*Primary Examiner*—Jill Warden
*Assistant Examiner*—S. G. Marshall
*Attorney, Agent, or Firm*—Richard R. Mybeck

[57] ABSTRACT

The synthesis of useful peptides presents a promising approach to new therapeutic agents. The Dolastatins, a series of linear and cyclic antineoplastic and/or cytostatic peptides isolated from Indian Ocean sea hare *Dolabella auricularia* represent excellent leads for synthetic modification.

The extraordinary inhibition of cell growth shown by the pentapeptideamides against six major types of human cancer has been presented. The intermediates of these reaction also show anticancer activity against the murine P388 lymphocytic leukemia cell line.

3 Claims, No Drawings

HUMAN CANCER INHIBITORY PENTAPEPTIDE AMIDES

Financial assistance for this project was provided by U.S. Government Grant Number OIG-CA44344-01-04; the United States Government may own certain rights to this invention.

INTRODUCTION

This invention relates generally to the field of antineoplastic compounds and more particularly to the synthesis of pentapeptide amides exhibiting antineoplastic effects.

BACKGROUND OF THIS INVENTION

Ancient marine invertebrate species of the *Phyla Bryozoa, Molluska*, and *Porifera* have been well established in the oceans for over one billion years. Such organisms have undergone trillions of biosynthetic reactions of their evolutionary chemistry to reach their present level of cellular organization, regulation and defense.

For example, marine sponges have changed minimally in physical appearance for nearly 500 million years. This suggests a very effective chemical resistance to evolution in response to changing environmental conditions over that period of time. Recognition of the potential for utilizing this biologically potent marine animal for medicinal purposes was recorded in Egypt about 2,700 BC and by 200 BC sea hare extracts were being used in Greece for their curative affect. This consideration along with the observation that marine animals, e.g. invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and antineoplastic and/or cytotoxic agents and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data approaches ten million dollars per compound. Economics dictate that such a huge investment be made only when there is a reasonable likelihood that it can be recovered. Absent such a likelihood, there will be no investment and, without investment, the research requisite for the discovery of these potentially life saving compounds will cease. Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989 for a description of the methods of statistical analysis. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The inhibition of human cancerous tumor growth as evidenced by NCI cell line data is utilitarian in that it relieves these conditions, thereby allowing the human thus afflicted to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of antineoplastic and tumor inhibiting activity as demonstrated by accepted NCI criteria as "utility" can promote research efforts in the United States and is unequivocally essential if those efforts are to obtain even a modest modicum of success.

BRIEF SUMMARY OF THE INVENTION

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from the Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide represents the most important member of the dolastatin family and is a potentially useful antineoplastic agent. Dolastatin 10 shows one of the best antineoplastic activity profiles against various cancer screens exhibited to date. The compounds disclosed herein are structural modification of dolastatin 10.

In the present patent application, as a first step the corresponding amine (2a–j) was allowed to react with Boc-L-phenylalanine (1). These amines were: 2-aminothiazole (2a); 2-amino-4-methylthiazole monohydrate (2b); 2-amino-4-phenylthiazole*HBr monohydrate (2c); 2-amino-1,3, 4,-thiadiazole (2d); 2-aminobenzothiazole (2e); 2-amino-6-methoxybenzothiazole(2f); 3-aminoquinoline(2g); 2-thiophenemethylamine (2h); 2-(aminomethyl)-pyridine (2i); 1-adamantane (2j). Synthesis of amides 3a–j using N,N-dicyclohexylcarbodiimide (DCC)/1-hydroxybenzotriazole (HOBt) or diethyl phosphorocyanidate (DEPC)/triethylamine or isobutyl chlorocarbonate/ N-methyl morpholine (NMM) for condensation led to excellent yields. No racemization was observed during these reactions.

The protecting group of amides 3a–j was removed with hydrogen chloride in acetic acid to afford the hydrochloride salt 4a–j. The correspondent deprotected-N-tert-butyloxycarbonyl-L-phenylalanineamide (4a–j) was coupled with dolaproine (5) in the presence of diethyl phosphorocyanidate and triethylamine yielding dipeptideamides 6a–j.

The protecting groups of amides 6a–j was removed with trifluoroacetic acid to afford the trifluoroacetate salt 7a–j. Diethyl phosphorocyanidate was used again with excellent results for coupling tripeptide trifluoroacetate 8 with each of the amide salts (7a–j) to yield Dolastatin 10 structural modifications 9a–j, which demonstrate extraordinary inhibition of cell growth.

Compound 9e and 9g has demonstrated an outstanding efficacy when administered to human tumor cell lines. For at least six cell lines compound 9e and 9g have a $GI_{50}$ of less than $10^{-7}$ µg/ml.

Accordingly the primary object of the subject invention is the synthesis of pentapeptide amide derivatives of dolastatin 10, and intermediates thereof, demonstrating extraordinary inhibition of cell growth and/or anti-cancer activity.

Another object of the subject invention is to discover the active portions of selected portions of dolastatin 10 derivatives that can be attached to other structures without loss of effectiveness.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide, represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was discovered. This compound has been tested in vivo and demonstrated significant activity, as shown below.

| Experimental Anticancer Activity of Dolastatin 10 in Murine in vivo Systems, T/C (µg/kg) | |
| --- | --- |
| P388 Lymphocytic Leukemia | L1210 Lymphocytic Leukemia |
| toxic (13.0) | 152 (13) |
| 155 and 17% cures (6.5) | 135 (6.5) |
| 146 and 17% cures (3.25) | 139 (3.25) |
| 137 (1.63) | 120 (1.63) |
| B16 Melanoma | Human Mammary Xenograph Nude Mouse |
| 238 and 40% cures (11.11) | Toxic (26) |
| 182 (6.67) | 137 (13) |
| 205 (4.0) | 178 (6.25) |
| 171 (3.4) | |
| 142 (1.44) | |
| M5076 Ovary Sarcoma | OVCAR-3 Human Ovary Xenograph Nude Mouse |
| toxic (26) | 300 (40) |
| 166 (13) | |
| 142 (6.5) | |
| 151 (3.25) | |
| LOX Human Melanoma Xenograph (Nude Mouse) | MX-1 Human Mammary Xenograft (Tumor Regression) |
| toxic (52) | 14 (52) |
| 301 and 67% cures (26) | 50 (26) |
| 301 and 50% cures (13) | 61 (13) |
| 206 and 33% cures (6.5) | 69 (6.25) |
| 170 and 17% cures (3.25) | |
| LOX in separate experiments | |
| 340 and 50% cures (43) | |
| 181 and 33% cures (26) | |
| 192 (15) | |

-continued

| Experimental Anticancer Activity of Dolastatin 10 in Murine in vivo Systems, T/C (μg/kg) |
|---|
| 138 and 17% cures (9.0) |

Dolastatin 10 has also been tested against a minipanel from the NCI Primary screen. These results appear below, showing the amount of Dolastatin 10 required to attain $GI_{50}$ in μg/ml, against the cell lines set forth below.

$$\frac{OVCAR-3}{9.5 \times 10^{-7}} (A) \quad \frac{SF\ 295}{7.6 \times 10^{-8}} (B) \quad \frac{A498}{2.6 \times 10^{-5}} (C)$$

$$\frac{NCI-H460}{3.4 \times 10^{-6}} (D) \quad \frac{KM2OL2}{4.7 \times 10^{-6}} (E) \quad \frac{SK-MEL-5}{7.4 \times 10^{-6}} (F)$$

From the foregoing, it can be seen that the in vitro activity of dolastatin 10 in the primary screen has been confirmed by in vivo animal tests.

For the minipanel, the following comparisons can be made Compound/Cell line 2-(4-phenylthiazole), 1-adamantane, 1,3,4-thiadiazole, 4-methylthiazole, 2-(benzothiazole), 2-(6-methoxybenzothiazole), 3-(aminoquinoline), 2-thiophenemethyl and 2-piridiyl-methyl terminal units.

In the present patent application, as a first step in the synthesis the corresponding amine (2a–j) was allowed to react with Boc-L- phenylalanine (1). These amines were: 2-aminothiazole (2a); 2-amino-4-methylthiazole monohydrate (2b); 2-amino-4-phenylthiazole*HBr monohydrate (2c); 2-amino-1,3, 4,-thiadiazole (2d); 2-aminobenzothiazole (2e); 2-amino-6-methoxybenzothiazole(2f); 3aminoquinoline(2g); 2-thiophenemethylamine (2h); 2-(aminomethyl)pyridine (2i); 1-adamantane (2j). Synthesis of amides 3a–j using N,N-dicyclohexylcarbodiimide (DCC)/1-hydroxybenzotriazole (HOBt) or diethyl phosphorocyanidate (DEPC)/ triethylamine or isobutyl chlorocarbonate/N-methyl morpholine (NMM) for condensation led to excellent yields. No racemization was observed during these reactions.

The protecting group of amides 3a–j was removed with hydrogen chloride in acetic acid to afford the hydrochloride salt 4a–j. The correspondent deprotected N-tert-butyloxycarbonyl-L-phenylalanineamide (4a–j) was coupled with dolaproine (5) in the presence of diethyl phosphorocyanidate and triethylamine yielding dipeptideamides 6a–j.

|  | A | B | C | D | E | F |
|---|---|---|---|---|---|---|
| Dola 10 | $9.5 \times 10^{-7}$ | $7.6 \times 10^{-8}$ | $2.6 \times 10^{-5}$ | $3.4 \times 10^{-6}$ | $4.7 \times 10^{-6}$ | $7.4 \times 10^{-6}$ |
| 9(e) | $3.3 \times 10^{-8}$ | $1.1 \times 10^{-7}$ | $2.3 \times 10^{-7}$ | $3.9 \times 10^{-10}$ | $2.6 \times 10^{-7}$ | $3.0 \times 10^{-9}$ |
| 9(g) | $4.6 \times 10^{-10}$ | $4.0 \times 10^{-8}$ | $1.0 \times 10^{-7}$ | $1.3 \times 10^{-8}$ | $3.9 \times 10^{-8}$ | $3.0 \times 10^{-9}$ |

For the compounds disclosed in this application, the in vitro tests disclosed in Tables 1a and 1b accordingly are reasonably accurate predictors of anticancer activity, and not mere indicators of the desirability for further testing.

Earlier a series of Dolastatin 10 chiral isomers was prepared. More recently these experiments were extended to the synthesis of (R)-Doe-isoDolastatin 10. The (R)-Dolaphenine (Doe) did not show any significant difference in its human cancer cell line activity as compared to Dolastatin 10. A new systematic series of modifications at the Dolaphenine position is disclosed.

This modification introduces a peptide bond between the phenylalanyl and 2-thiazole moiety obtaining pentapeptideamide-N-(2-thiazole). The importance of the 2-thiazole residue was evaluated by replacing it with The protecting groups of amides 6a–j was removed with trifluoroacetic acid to afford the trifluoroacetate salt 7a–j.

Diethyl phosphorocyanidate was used again with excellent results for coupling tripeptide trifluoroacetate 8 with each of the amide salts (7a–j) to yield Dolastatin 10 structural modifications 9a–j. The above scheme is shown below as Scheme 1. The extraordinary inhibition of cell growth shown by the pentapeptideamides 9a–j against six major types of human cancer has been presented in Tables 1a and 1b.

SCHEME I

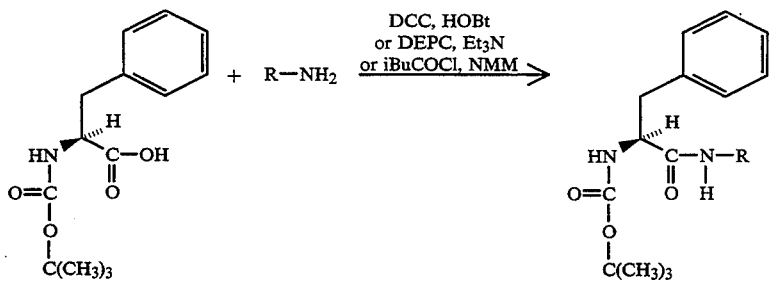

-continued
SCHEME I
2b R = 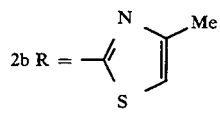   3b R = 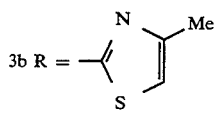
2c R = 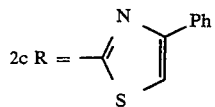   3c R = 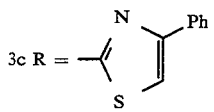
2d R = 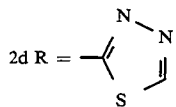   3d R = 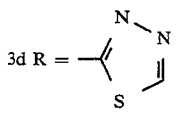
2e R = 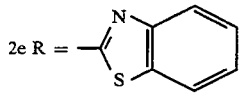   3e R = 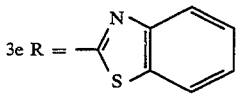
2f R = 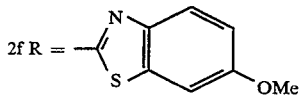   3f R = 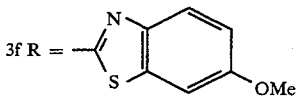
2g R = 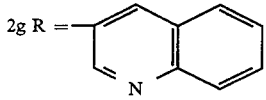   3g R = 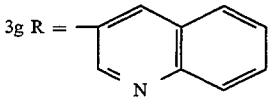
2h R = 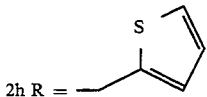   3h R = 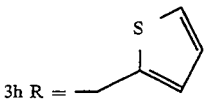
2i R = 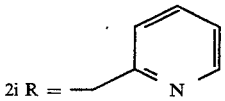   3i R = 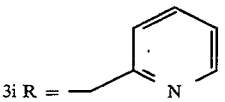
2j R = 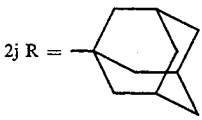   3j R = 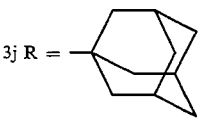
DCC = N,N-dicyclohexylcarbodiimide
HOBt = 1-hydroxybenzotriazole
DEPC = diethyl phosphorocyanidate
NMM = N-methyl morpholine
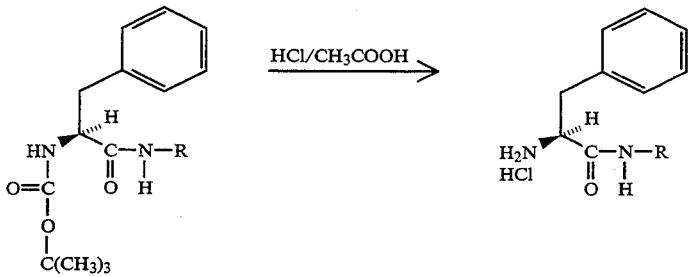
3a R = 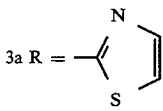   4a R = 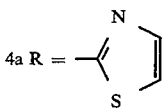

-continued
SCHEME I
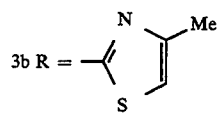 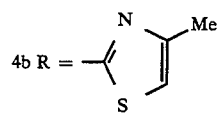
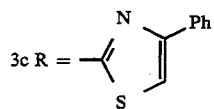 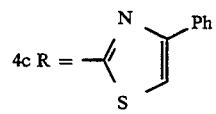
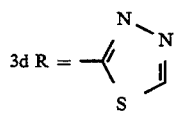 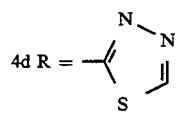
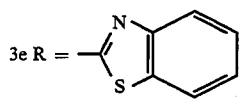 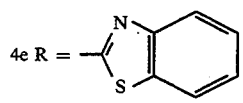
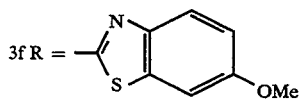 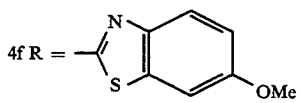
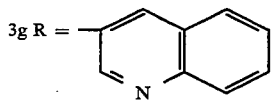 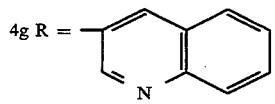
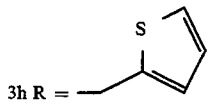 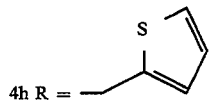
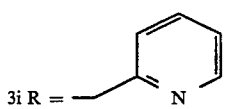 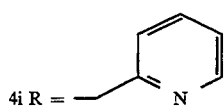
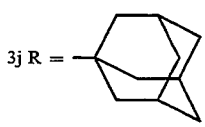 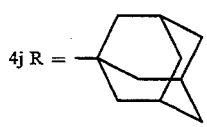
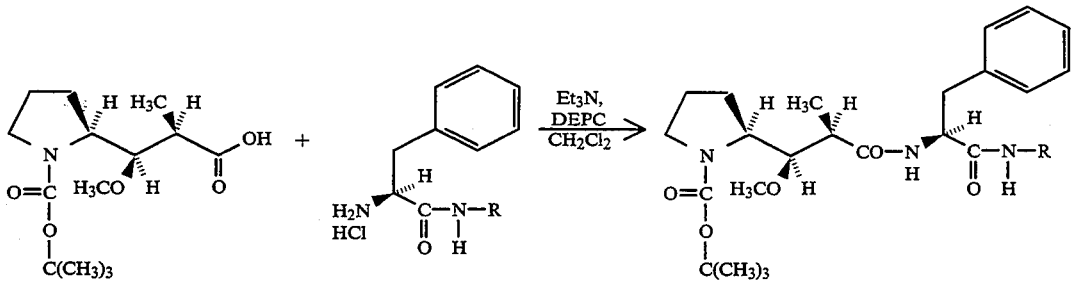
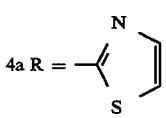 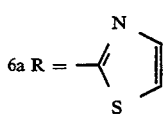

-continued
SCHEME I
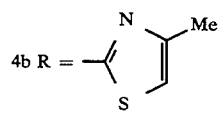 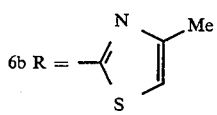
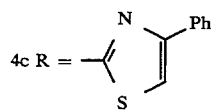 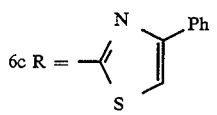
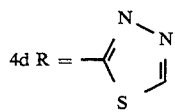 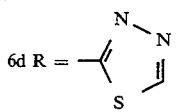
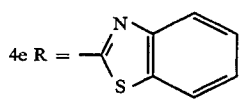 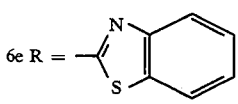
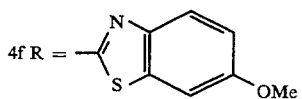 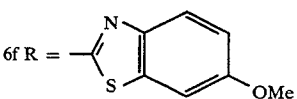
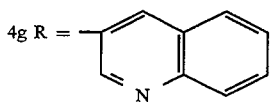 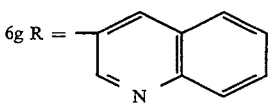
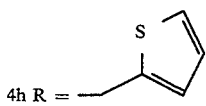 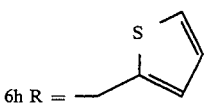
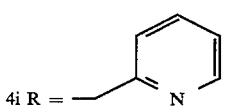 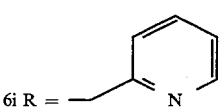
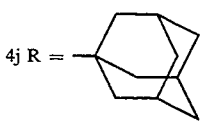 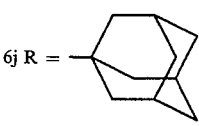
DEPC = diethyl phosphorocyanidate
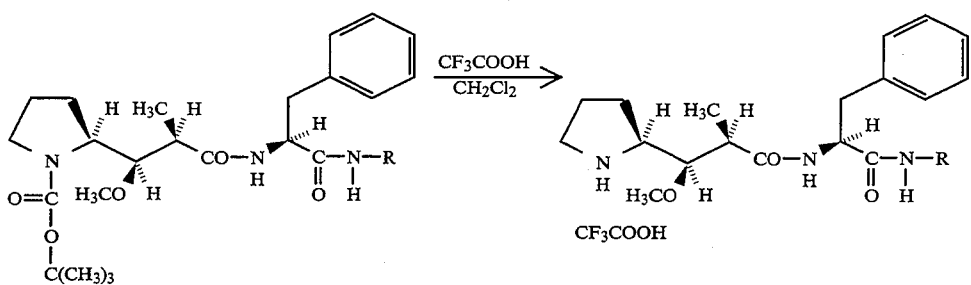
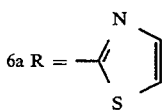 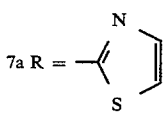

-continued
SCHEME I
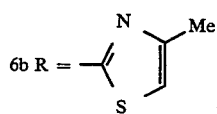 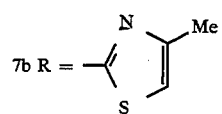
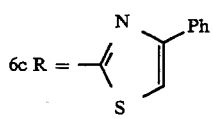 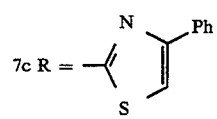
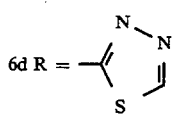 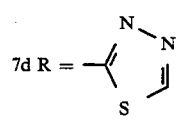
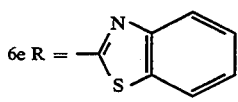 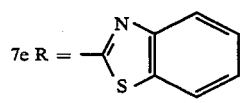
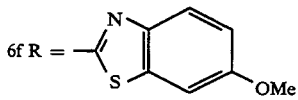 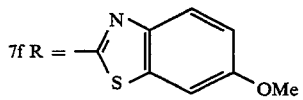
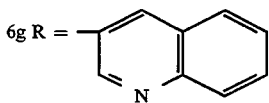 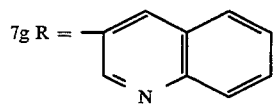
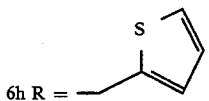 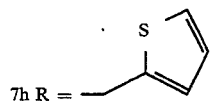
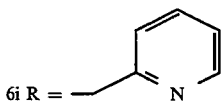 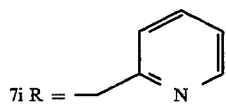
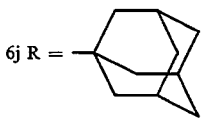 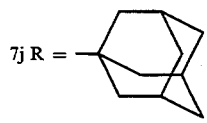
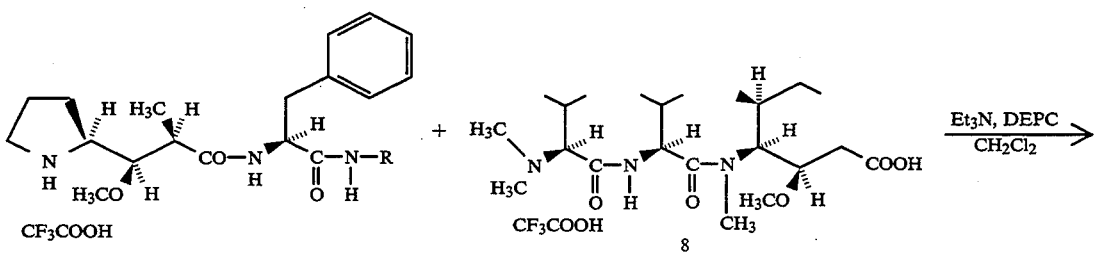

-continued
SCHEME I
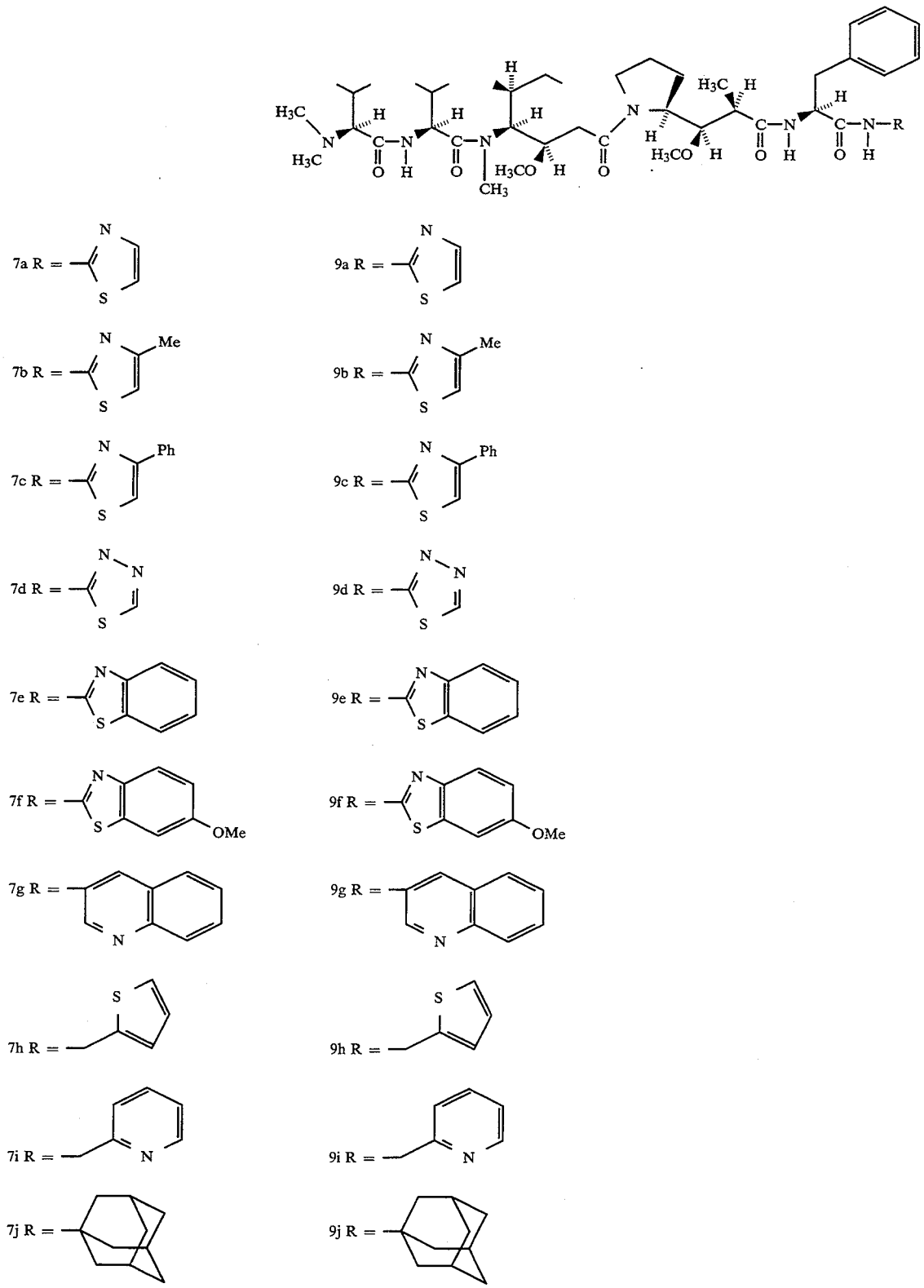
DEPC = diethyl phosphorocyanidate

TABLE 1a

The Cancer Cell Growth Inhibitory Activity of Pentaptideamides 9a–e on Human Cancer Cell Lines

| | Cell type | Cell line | 9a | 9b | 9c | 9d | 9e |
|---|---|---|---|---|---|---|---|
| GI-50 (µg/ml) | Ovarian | OVCAR-3 | 0.0000005 | 0.00000020 | 0.000020 | 0.0000031 | 0.000000033 |
| | CNS | SF-295 | 0.0000038 | 0.0000026 | 0.000065 | 0.000024 | 0.00000011 |
| | Renal | A498 | 0.0000056 | 0.0000053 | 0.000057 | 0.000039 | 0.00000023 |
| | Lung-NSC | NCI-H460 | 0.0000018 | 0.00000046 | 0.000056 | 0.0000036 | 0.000000039 |
| | Colon | KM20L2 | 0.0000020 | 0.0000034 | 0.00020 | 0.0000099 | 0.00000026 |
| | Melanoma | SK-MEL-5 | 0.0000014 | 0.00000081 | 0.000043 | 0.0000082 | 0.000000030 |
| TGI (µg/ml) | Ovarian | OVCAR-3 | 0.0000044 | 0.000012 | 0.00013 | 0.00016 | 0.00000019 |
| | CNS | SF-295 | >0.0001 | >0.0001 | >0.001 | >0.0001 | 0.00000096 |
| | Renal | A498 | 0.000090 | >0.0001 | 0.00072 | >0.0001 | >0.000001 |
| | Lung-NSC | NCI-H460 | 0.0000090 | 0.000013 | 0.00051 | 0.000061 | 0.00000044 |
| | Colon | KM20L2 | 0.000011 | 0.000017 | 0.00075 | 0.000015 | 0.00000070 |
| | Melanoma | SK-MEL-5 | 0.000080 | >0.0001 | 0.00033 | 0.0000070 | >0.000001 |
| LC-50 (µg/ml) | Ovarian | OVCAR-3 | 0.000088 | >0.0001 | >0.001 | >0.0001 | >0.000001 |
| | CNS | SF-295 | >0.0001 | >0.0001 | >0.001 | >0.0001 | >0.000001 |
| | Renal | A498 | >0.0001 | >0.0001 | >0.001 | >0.0001 | >0.000001 |
| | Lung-NSC | NCI-H460 | >0.0001 | >0.0001 | >0.001 | >0.0001 | >0.000001 |
| | Colon | KM20L2 | >0.0001 | >0.0001 | >0.001 | 0.00069 | >0.000001 |
| | Melanoma | SK-MEL-5 | >0.0001 | >0.0001 | >0.001 | 0.00043 | >0.000001 |

TABLE 1b

The Cancer Cell Growth Inhibitory Activity of Pentaptideamides 9f–j on Human Cancer Cell Lines

| | Cell type | Cell line | 9f | 9g | 9h | 9i | 9j |
|---|---|---|---|---|---|---|---|
| GI-50 (µg/ml) | Ovarian | OVCAR-3 | 0.00032 | 0.00000000046 | <0.000001 | 0.000056 | 0.000019 |
| | CNS | SF-295 | 0.00055 | 0.000000040 | 0.00014 | 0.00036 | 0.000030 |
| | Renal | A498 | 0.00037 | 0.000000100 | 0.000055 | 0.00059 | 0.000034 |
| | Lung-NSC | NCI-H460 | 0.00033 | 0.000000013 | 0.0000089 | 0.000051 | 0.000014 |
| | Colon | KM20L2 | 0.00036 | 0.000000039 | 0.000049 | 0.00033 | 0.000027 |
| | Melanoma | SK-MEL-5 | 0.000090 | 0.0000000030 | <0.000001 | 0.000029 | 0.000022 |
| TGI (µg/ml) | Ovarian | OVCAR-3 | 0.0011 | 0.000000079 | 0.00028 | 0.0020 | 0.000055 |
| | CNS | SF-295 | >0.01 | 0.00000061 | >0.01 | >0.01 | >0.0001 |
| | Renal | A498 | >0.01 | >0.000001 | 0.0069 | >0.01 | >0.0001 |
| | Lung-NSC | NCI-H460 | 0.0016 | 0.00000012 | 0.00037 | 0.0010 | 0.000057 |
| | Colon | KM20L2 | 0.0022 | 0.00000023 | 0.0013 | >0.01 | 0.000072 |
| | Melanoma | SK-MEL-5 | >0.01 | >0.000001 | >0.01 | >0.01 | >0.0001 |
| LC-50 (µg/ml) | Ovarian | OVCAR-3 | >0.01 | >0.000001 | 0.0097 | >0.01 | >0.0001 |
| | CNS | SF-295 | >0.01 | >0.000001 | >0.01 | >0.01 | >0.0001 |
| | Renal | A498 | >0.01 | >0.000001 | >0.01 | >0.01 | >0.0001 |
| | Lung-NSC | NCI-H460 | >0.01 | >0.000001 | >0.01 | >0.01 | >0.0001 |
| | Colon | KM20L2 | >0.01 | >0.000001 | >0.01 | >0.01 | >0.0001 |
| | Melanoma | SK-MEL-5 | >0.01 | >0.000001 | >0.01 | >0.01 | >0.0001 |

To further aid in the understanding of the present invention, and not by way of limitation the following examples are presented.

EXAMPLE I-1

The Synthesis of Phenylalanineamides 3a–j.

General Procedure A

To a solution of N-tert-butyloxycarbonyl-L-phenylalanine (1, 2.6 g, 10 mmol) and 1-hydroxybenzotriazole (1.5 g, 11 mmol) in dry tetrahydrofurane (20 mL) was added the respective amine 2 (11 mmol) followed by N,N-dicyclohexylcarbodiimide (2.2 g, 11 mmol) and the solution was stirred under argon for one hour at 0° C. and one hour at room temperature, additional N,N-dicyclohexyl-carbodiimide (1.1 g, 6 mmol) in dry tetrahydrofurane (10 mL) added and stirring continued for additional 2 hours at room temperature. The N,N'-dicyclohexyl urea was removed by filtration and the solvent was removed (under vacuum at room temperature). The oily product was dissolved in ethyl acetate (300 mL) and organic phase washed with potassium hydrogen sulfate (10% aq., 100 mL), water (100 mL), saturated aqueous sodium hydrogen carbonate (100 mL) and dried over sodium sulfate. Solvent was removed in vacuum and the residue was chromatographed [SILICA GEL (0.040–0.063 mm) column]. After evaporation of the solvent from the fractions (selected by thin layer chromatography) the residue was dried in a desiccator under vacuum overnight to afford the amide (3) as oily product which was crystallized from diethyl ether-n-hexane to yield white crystals.

EXAMPLE I-a

Synthesis of N-tert-butyloxycarbonyl-L-phenylalanine-N-(2-thiazole) general (3a)

Compound 3a was synthesized from N-tert-butyloxycarbonyl-L-phenylalanine (1) and 2-aminothiazole (2a) according to General Procedure A. The reaction mixture was purified via column chromatography by use of SILICA GEL with n-hexane-ethyl acetate (1:1) as eluent.

Yield 3a: 3.23 g (93.0%)
$[\alpha]_D^{25} = -38.6°$ (c=1.06 in $CHCl_3$)
M.p.: 131°–132° C.

EXAMPLE I-b

Synthesis of N-tert-butyloxycarbonyl-L-phenylalanine-N-[2-(4-methylthiazole)] compound (3b)

Compound 3b was synthesized from N-tert-butyloxycarbonyl-L-phenylalanine (1) and 2-amino-4-methylthiazole monohydrate (2b) according to General Procedure A. The reaction mixture was purified via column chromatography by use of SILICA GEL with n-hexane-ethyl acetate (1:1) as eluent.

Yield 3b: 3.26 g (90.1%)
$[\alpha]_D^{25} = -45.78°$ (c=2.23 in CHCl$_3$)
M.p.: 120°–122° C.

EXAMPLE I-c

Synthesis of N-tert-butyloxycarbonyl-L-phenylalanine-N-[2-(4-phenylthiazole)] compound (3c)

Compound 3c was synthesized from N-tert-butyloxycarbonyl-L-phenylalanine (1), 2-amino-4-phenylthiazole*HBr monohydrate (2c) and triethylamine according to General Procedure A. The reaction mixture was purified via column chromatography by use of SILICA GEL with n-hexane-ethyl acetate (2:1) as eluent.

Yield 3c: 3.96 g (93.6%)
$[\alpha]_D^{25} = -2.8°$ (c=0.56 in CHCl$_3$)
M.p.: 199°–201° C.

EXAMPLE I-d

Synthesis of N-tert-butyloxycarbonyl-L-phenylalanine -N-[2-(1,3,4 -thiadiazole)] compound (3d)

Compound 3d was synthesized from N-tert-butyloxycarbonyl-L-phenylalanine (1) and 2-amino-1,3,4-thiadiazole (2d) according to General Procedure A. The reaction mixture was purified via column chromatography by use of SILICA GEL with n-hexane-ethyl acetate (1:1) as eluent.

Yield 3d: 2.59 g (74.3%)
$[\alpha]_D^{25} = -70.79°$ (c=1.01 in CHCl$_3$)
M.p.: 93°–95° C.

EXAMPLE I-e

Synthesis of N-tert-butyloxycarbonyl-L-phenylalanine-N-(2-benzothiazole) compound (3e)

Compound 3e was synthesized from N-tert-butyloxycarbonyl-L-phenylalanine (1) and 2-aminobenzothiazole (2e) according to General Procedure A. The reaction mixture was purified via column chromatography by use of SILICA GEL with n-hexane-ethyl acetate (5:4) as eluent.

Yield 3e: 2.98 g (74.9%) $[\alpha]_D^{25} = -72.92°$ (c=2.43 in CHCl$_3$)
M.p.: 141°–143° C.

EXAMPLE I-f

Synthesis of N-tert-butyloxycarbonyl-L-phenylalanine-N-[2-(6-methoxybenzothiazole)] compound (3f)

Compound 3f was synthesized from N-tert-butyloxycarbonyl-L-phenylalanine (1) and 2-amino-6-methoxybenzothiazole (2f) according to General Procedure A. The reaction mixture was purified via column chromatography by use of SILICA GEL with n-hexane-ethyl acetate (5:4) as eluent.

Yield 3f: 3.04 g (71.1%)
$[\alpha]_D^{25} = -63.77°$ (c=1.30 in CHCl$_3$)
M.p.: 130°–132° C.

EXAMPLE I-g

Synthesis of N-tert-butyloxycarbonyl-L-phenylalanine-N-(3-quinoline) compound (3g)

Compound 3g was synthesized from N-tert-butyloxycarbonyl-L-phenylalanine (1) and 3-aminoquinoline (2g) according to General Procedure A. The reaction mixture was purified via column chromatography by use of SILICA GEL with n-hexane-ethyl acetate (1:1) as eluent.

Yield 3g: 2.86 g (73.0%)
$[\alpha]_D^{25} = -16.38°$ (c=0.83 in CHCl$_3$)
M.p.: 143°–145° C.

EXAMPLE I-2

General Procedure B

A solution of N-tert-Butyloxycarbonyl-L-Phenylalanine (2.65 g, 10 mmol) in dry tetrahydrofurane (40 mL) is cooled to −15° C. and neutralized with N-methylmorpholine (1.01 g, 10 mmol). Isobutyl chlorocarbonate (1.37 g, 10 mmol) is added, followed, about one minute later by the solution of amine 2 (10 mmol) in dry tetrahydrofurane (10 mL). The reaction mixture is allowed to warm up to room temperature. The precipitated N-methylmorpholine hydrochloride is removed by filtration and washed with tetrahydrofurane. Solvent is removed in vacuum and residue dissolved in ethyl acetate (300 mL). The organic layer was washed with potassium hydrogen sulfate (10%, 50 mL), water (50 mL), saturated aqueous sodium hydrogen carbonate solution (50 mL), water (50 mL) and dried over sodium sulfate. Solvent is removed in vacuum to about 10 mL and n-hexane (50 mL) added. The product crystalize as a white powder.

EXAMPLE I-h

Synthesis of N-tert-butyloxycarbonyl-L-phenylalanine-N-(methenyl-2-thiophene) compound (3h)

Compound 3h was synthesized from N-tert-butyloxycarbonyl-L-phenylalanine (1) and 2-thiophenemethylamine (2h) according to General Procedure B.

Yield 3h: 2.95 g (81.9%)
$[\alpha]_D^{25} = -1.04°$ (c=0.67 in CHCl$_3$)
M.p.: 117°–119° C.

EXAMPLE I-i

Synthesis of N-tert-butyloxycarbonyl-L-phenylalanine-N-(methenyl-2-pyridine) compound (3i)

Compound 3i was synthesized from N-tert-butyloxycarbonyl-L-phenylalanine (1) and 2-(aminomethyl)-pyridine (2i) according to General Procedure B.

Yield 3i: 2.50 g (70.3%)
$[\alpha]_D^{25} = -7.86°$ (c=0.56 in CHCl$_3$)
M.p.: 115°–117° C.

EXAMPLE I-3

General Procedure C

N-tert-Butyloxycarbonyl-L-Phenylalanine (265 mg, 1 mmol) dissolved in methylene chloride (10 mL) then triethylamine (0.20 g, 2 mmol) added followed with amine 2 (151 mg, 1 mmol). The solution was cooled in an ice-water bath and diethyl cyanophosphonate (0.16 g, 1 mmol) added. The reaction mixture was stirred for 3 h at 0° C., then diluted with methylene chloride (100 mL). The organic layer was washed with citric acid (10%, 40 mL), water (40 mL), saturated aqueous sodium hydrogen carbonate solution (40 mL), water (40 mL) and dried (sodium sulfate). The product was purified on "flash" SILICA GEL (0.040–0.063 mm) column to yield oily product which was crystallized from diethyl ether-n-hexane to afford white crystals.

EXAMPLE I-j

Synthesis of N-tert-butyloxycarbonyl-L-phenylalanine-N-(1-adamantane) compound (3j)

Compound 3j was synthesized from N-tert-butyloxycarbonyl-L-phenylalanine (1) and 1-adamantone (2j) according to General Procedure C. The reaction mixture was purified via column chromatography by use of SILICA GEL with n-hexane-ethyl acetate (7:3) as eluent.

Yield 3j: 3.53 g (88.6%)
$[\alpha]_D^{25} = +4.0°$ (c=0.62 in CHCl$_3$)
M.p.: 95°–96° C.

EXAMPLE II

The Deprotection of Phenylalanineamides 3a–j for obtaining hydrogen chloride salt 4a–j.

General Procedure D

A solution of the Phenylalanineamide 3a–j (2 mmol) in hydrogen chloride/acetic acid (1.0M hydrogen chloride, 30 mL) was stirred at 10° C. for half hour. The solvent was removed under reduced pressure. The residue dissolved in toluene, solvent removed in vacuum and triturated with diethylether. Crystals were filtered and dried in vacuum desiccator to afford the respective hydrogenchloride salt 4a–j.

EXAMPLE III

The Synthesis of Boc-Dipeptideamides 6a–j.

General Procedure E

To a solution of [2S-[2R*($\alpha$S*,$\beta$S*)]]-1-[(1,1-dimethylethoxy) carbonyl]-$\beta$-methoxy-$\alpha$-methyl-2-pyrrolidinepropanoic acid (Boc-Dolaproine, 5, 287 mg, 1 mmol) in dry methylene chloride (3 mL, distilled from calcium hydride) was added the respective amide hydrogen chloride salt (4a–j, 1 mmol) followed by triethylamine (0.154 mL, 2 mmol) and diethyl phosphorocyanidate (0.09 mL, 93%, 1 mmol, ice bath) and the solution was stirred under vacuum for two hours. The solvent was removed (under vacuum at room temperature) and the residue was chromatographed [SILICA GEL (0.040–0.063 mm) column]. After the evaporation of solvent from the fractions (selected by thin layer chromatography) 2 mL dry methylene chloride was added and evaporation was repeated. The residue was dried in a desiccator under vacuum overnight to afford the amide (6a–j) as a viscous oil, which was triturated from diethyl ether obtaining white crystals.

EXAMPLE IV

The Deprotection of Boc-Dipeptideamides 6a–j obtaining trifluoroacetate salt 7a–j.

General Procedure F

A solution of the dipeptideamide 6a–j (1 mmol) in methylene chloride (2 mL) and trifluoroacetic acid (2 mL) was stirred (ice bath under an argon atmosphere) for 30 min. The solvent was removed under reduced pressure and toluene was added to the residue. Solvent was again removed in vacuum and this operation was repeated. The residue was dried in a desiccator (under vacuum overnight) to afford the trifluoroacetate salt 7a–j as a viscous oil, which was triturated with diethyl ether obtaining white solid.

EXAMPLE V

The Synthesis of Pentapeptideamides 9a–j.

General Procedure G

To a solution of the trifluoroacetate salt 7a–j (0.2 mmol) in methylene chloride (2 mL, distilled from calcium hydride) was added the tripeptide trifluoroacetate salt (8, 0.109 g, 0.2 mmol) followed by triethylamine (0.088 mL, 0.63 mmol) and diethyl phosphorocyanidate (0.036 mL, 93%, 0.22 mmol, ice bath). The solution was stirred under argon for two hours. The solvent was removed (under vacuum at room temperature) and the residue was chromatographed [SILICA GEL (0.040–0.063 mm)] column. After the evaporation of solvent from the fractions (selected by thin layer chromatography) 2 mL of dry methylene chloride was added followed with 10 mL of n-hexane and evaporated under a stream of argon to yield a white fluffy solid.

EXAMPLE VI

Synthesis of L-Dolavalyl-L-Valyl-N-Methyl-(S,S,R)-Dolaisoleucyl-(S,R,R)-Dolaproyl-L-Phenylalanineamide-N-(2-thiazole) compound (9a)

Compound 4a was synthesized from N-tert-butyloxycarbonyl-L-phenylalanine -N-(2-thiazole) (3a) according to General Procedure D.

Yield 4a: 0.558 g (98.3%)
$[\alpha]_D^{25} = +110°$ (c=0.2 in CH$_3$OH)
M.p.: 197°–198° C.

Compound 6a was synthesized from Boc-dolaproine (5) and L-Phenylalanine-N-(2-thiazole) hydrochloride (4a) according to General Procedure E. The reaction mixture was purified via column chromatography by use of SILICA GEL with n-hexane-toluene-isopropanol (6:1:1) as eluent.

Yield 6a: 0.457 g (88.6%) $[\alpha]_D^{25} = -82.9°$ (c=0.48 in CHCl$_3$)
M.p.: 92°–93° C.

Compound 7a was synthesized according to General Procedure F.

Yield 7a: 0.522 g (98.3%) $[\alpha]_D^{25} = -21.3°$ (c=0.23 in CH$_3$OH)
M.p.: 98°–99° C.

Compound 9a was synthesized from tripeptide (8) and (S,R,R)-Dolaproinyl-L-Phenylalanineamide-N-(2-thiazole) trifluoroacetate (7a) according to General Procedure G. The reaction mixture was purified via column chromatography by use of SILICA GEL with n-hexane-acetone (2:3) as eluent.

Yield 9a: 0.140 g (84.7%)
$[\alpha]_D^{25} = -27.6°$ (c=0.2 in CHCl$_3$)
M.p.: 124°–125° C.

EXAMPLE VII

Synthesis of L-Dolavalyl-L-Valyl-N-Methyl-(S,S,R)-Dolaisoleucyl-(S,R,R)-Dolaproyl-L-Phenylalanineamide-N-[2-(4-methylthiazole)] compound (9b)

Compound 4b was synthesized from N-tert-butyloxycarbonyl-L-phenylalanine-N-[2-(4-methylthiazole)] (3b) according to General Procedure D.

Yield 4b: 0.585 g (98.2%)
$[\alpha]_D^{25} = +68.70°$ (c=0.69 in CH$_3$OH)
M.p.: 216°–218° C.

Compound 6b was synthesized from Boc-dolaproine (5) and L-Phenylalanine-N-[2-(4-methylthiazole)] hydrochloride (4b) according to General Procedure E. The reaction mixture was purified via column chromatography by use of SILICA GEL with n-hexane-acetone (3:1) as eluent.

Yield 6b: 0. 490 g (92.4%)

$[\alpha]_D^{25} = -73.93°$ (c=0.61 in CHCl$_3$)
M.p.: 76°-78° C.

Compound 7b was synthesized according to General Procedure F.
  Yield 7b: 0.535 g (98.2%)
  $[\alpha]_D^{25} = -55.0°$ (c=0.14 in CHCl$_3$)
  M.p.: 79°-81° C.

Compound 9b was synthesized from tripeptide (8) and (S,R,R)-Dolaproinyl-L-Phenylalanineamide-N-[2-(4-methylthiazole)]trifluoroacetate (7b) according to General Procedure G. The reaction mixture was purified via column chromatography by use of SILICA GEL with n-hexane-acetone (1:1) as eluent.
  Yield 9b: 0.153 g (91.1%)
  $[\alpha]_D^{25} = -38.62°$ (c=0.29 in CHCl$_3$)
  M.p.: 118°-120° C.

EXAMPLE VIII

Synthesis of L-Dolavalyl-L-Valyl-N-Methyl-(S,S,R)-Dolaisoleucyl-(S,R,R)-Dolaproyl-L-Phenylalanineamide-N-[2-(4-phenylthiazole)] compound (9c)

Compound 4c was synthesized from N-tert-butyloxycarbonyl-L-phenylalanine-N-[2-(4-phenylthiazole)] (3c) according to General Procedure D.
  Yield 4c: 0.708 g (98.4%)
  $[\alpha]_D^{25} = +30.4°$ (c=0.25 in CH$_3$OH)
  M.p.: 173°-175° C.

Compound 6c was synthesized from Boc-dolaproine (5) and L-Phenylalanine-N-[2-(4-phenylthiazole)] hydrochloride (4c) according to General Procedure E. The reaction mixture was purified via column chromatography by use of SILICA GEL with n-hexane-acetone (3:1) as eluent.
  Yield 6c: 0.532 g (89.7%)
  $[\alpha]_D^{25} = -56.9°$ (c=0.13 in CHCl$_3$)
  M.p.: 86°-88° C.

Compound 7c was synthesized according to General Procedure F.
  Yield 7c: 0.598 g (98.7%)
  $[\alpha]_D^{25} = -54.6°$ (c=0.13 in CHCl$_3$)
  M.p.: 108°-110° C.

Compound 9c was synthesized from tripeptide (8) and (S,R,R)-Dolaproinyl-L-Phenylalanineamide-N-[2-(4-phenylthiazole) trifluoroacetate (7c) according to General Procedure G. The reaction mixture was purified via column chromatography by use of SILICA GEL with n-hexane-acetone (3:2) as eluent.
  Yield 9c: 0.163 g (90.3%)
  $[\alpha]_D^{25} = -57.3°$ (c=0.11 in CHCl$_3$)
  M.p.: 136°-138° C.

EXAMPLE IX

Synthesis of L-Dolavalyl-L-Valyl-N-Methyl-(S,S,R)-Dolaisoleucyl-(S,R,R)-Dolaproyl-L-Phenylalanineamide-N-[2-(1,3,4-thiadiazole)] compound (9d)

Compound 4d was synthesized from N-tert-butyloxycarbonyl-L-phenylalanine-N-[2-(1,3,4-thiadiazole)] (3d) according to General Procedure D.
  Yield 4d: 0.559 g (98.1%)
  $[\alpha]_D^{25} = +79.06°$ (c=0.53 in CH$_3$OH)
  M.p.: 188°-190° C.

Compound 6d was synthesized from Boc-dolaproine (5) and L-Phenylalanine-N-[2-(1,3,4-thiadiazole)] hydrochloride (4d) according to General Procedure E. The reaction mixture was purified via column chromatography by use of SILICA GEL with n-hexane-acetone (3:2) as eluent.
  Yield 6d: 0.432 g (83.5%)
  $[\alpha]_D^{25} = -80.0°$ (c=0.21 in CHCl$_3$)
  M.p.: 108°-110° C.

Compound 7d was synthesized according to General Procedure F.
  Yield 7d: 0.527 g (99.1%)
  $[\alpha]_D^{25} = -53.33°$ (c=0.12 in CHCl$_3$)
  M.p.: 120°-122° C.

Compound 9d was synthesized from tripeptide (8) and (S,R,R)-Dolaproinyl-L-Phenylalanineamide-N-[2-(1,3,4-thiadiazole)]trifluoroacetate (7d) according to General Procedure G. The reaction mixture was purified via column chromatography by use of SILICA GEL with n-hexane-acetone (2:1) as eluent.
  Yield 9d: 0.158 g (95.4%)
  $[\alpha]_D^{25} = -12.3°$ (c=0.39 in CHCl$_3$)
  M.p.: 151°-153° C.

EXAMPLE X

Synthesis of L-Dolavalyl-L-Valyl-N-Methyl-(S,S,R)-Dolaisoleucyl-(S,R,R)-Dolaproyl-L-Phenylalanineamide-N-(2-benzothiazole) compound (9e)

Compound 4e was synthesized from N-tert-butyloxycarbonyl-L-phenylalanine-N-(2-benzothiazole) (3e) according to General Procedure D.
  Yield 4e: 0.650 g (97.3%)
  $[\alpha]_D^{25} = +99.95°$ (c=0.22 in CH$_3$OH)
  M.p.: 215°-217° C.

Compound 6e was synthesized from Boc-dolaproine (5) and L-Phenylalanine-N-(2-benzothiazole) hydrochloride (4e) according to General Procedure E. The reaction mixture was purified via column chromatography by use of SILICA GEL with n-hexane-acetone (3:1) as eluent.
  Yield 6e: 0.462 g (81.5%)
  $[\alpha]_D^{25} = -83.0°$ (c=0.1 in CHCl$_3$)
  M.p.: 104°-106° C.

Compound 7e was synthesized according to General Procedure F.
  Yield 7e: 0.569 g (98.0%)
  $[\alpha]_D^{25} = -65.0°$ (c=0.1 in CHCl$_3$)
  M.p.: 133°-135° C.

Compound 9e was synthesized from tripeptide (8) and (S,R,R)-Dolaproinyl-L-Phenylalanineamide-N-(2-benzothiazole) trifluoroacetate (7e) according to General Procedure G. The reaction mixture was purified via column chromatography by use of SILICA GEL with n-hexane-acetone (3:2) as eluent.
  Yield 9e: 0.143 g (81.3%)
  $[\alpha]_D^{25} = -36.66°$ (c=0.18 in CHCl$_3$)
  M.p.: 153°-155° C.

EXAMPLE XI

Synthesis of L-Dolavalyl-L-Valyl-N-Methyl-(S,S,R)-Dolaisoleucyl-(S,R,R)-Dolaproyl-L-Phenylalanineamide-N-[2-(6-methoxybenzo-thiazole)] compound (9f)

Compound 4f was synthesized from N-tert-butyloxycarbonyl-L-phenylalanine-N-[2-(6-methoxybenzothiazole)] (3f) according to General Procedure D.
  Yield 4f: 0.679 g (97.6%)
  $[\alpha]_D^{25} = +134.71°$ (c=0.17 in CH$_3$OH)
  M.p.: 218°-220° C.

Compound 6f was synthesized from Boc-dolaproine (5) and L-Phenylalanine-N-[2-(6-methoxybenzothiazole)] hydrochloride (4f) according to General Procedure E. The reaction mixture was purified via column chromatography by use of SILICA GEL with n-hexane-acetone (3:1) as eluent.
  Yield 6f: 0.515 g (86.3%)

$[\alpha]_D^{25} = -81.06°$ (c=0.47 in CHCl$_3$)
M.p.: 98°–100° C.

Compound 7f was synthesized according to General Procedure F.

Yield 7f: 0.603 g (98.7%)
$[\alpha]_D^{25} = -56.19°$ (c=0.21 in CHCl$_3$)
M.p.: 116°–118° C.

Compound 9f was synthesized from tripeptide (8) and (S,R,R)-Dolaproinyl-L-Phenylalanineamide-N-[2-(6-methoxybenzothiazole)] trifluoroacetate (7f) according to General Procedure G. The reaction mixture was purified via column chromatography by use of SILICA GEL with n-hexane-acetone (3:2) as eluent.

Yield 9f: 0.159 g (87.6%)
$[\alpha]_D^{25} = -49.22°$ (c=0.51 in CHCl$_3$)
M.p.: 168°–170° C.

EXAMPLE XII

Synthesis of L-Dolavalyl-L-Valyl-N-Methyl-(S,S,R)-Dolaisoleucyl-(S,R,R)-Dolaproyl-L-Phenylalaninea-mide-N-(3-quinoline) compound (9g)

Compound 4g was synthesized from N-tert-butyloxycarbonyl-L-phenylalanine-N-(3-quinoline) (3g) according to General Procedure D.

Yield 4g: 0.643 g (98.1%)
$[\alpha]_D^{25} = +102.11°$ (c=0.52 in CH$_3$OH)
M.p.: 184°–186° C.

Compound 6g was synthesized from dolaproine (5) and L-Phenylalanine-N-(3-quinoline) hydrochloride (4g) according to General Procedure E. The reaction mixture was purified via column chromatography by use of SILICA GEL with n-hexane-acetone (3:2) as eluent.

Yield 6g: 0.442 g (78.9%)
$[\alpha]_D^{25} = -79.5°$ (c=0.2 in CHCl$_3$)
M.p.: 184°–185° C.

Compound 7g was synthesized according to General Procedure F.

Yield 7g: 0.566 g (98.5%)
$[\alpha]_D^{25} = -38.13°$ (c=0.32 in CHCl$_3$)
M.p.: 133°–135° C.

Compound 9g was synthesized from tripeptide (8) and (S,R,R)-Dolaproinyl-L-Phenylalanineamide-N-(3-quinoline) trifluoroacetate (7g) according to General Procedure G. The reaction mixture was purified via column chromatography by use of SILICA GEL with D-hexane-acetone (2:1) as eluent.

Yield 9g: 0.145 g (82.9%)
$[\alpha]_D^{25} = -75.83°$ (c=0.12 in CHCl$_3$)
M.p.: 172°–174° C.

EXAMPLE XIII

Synthesis of L-Dolavalyl-L-Valyl-N-Methyl-(S,S,R)-Dolaisoleucyl-(S,R,R)-Dolaproyl-L-Phenylalaninea-mide-N-(methenyl-2-thiophene) compound (9h)

Compound 4h was synthesized from N-tert-butyloxycarbonyl-L-phenylalanine-N-(methenyl-2-thiophene) (3h) according to General Procedure D.

Yield 4h: 0.585 g (98.5%)
$[\alpha]_D^{25} = -+20.50°$ (c=0.6 in CH$_3$OH)
M.p.: 165°–166° C.

Compound 6h was synthesized from Boc-dolaproine (5) and L-Phenylalanine-N-(methenyl-2-thiophene) hydrochloride (4h) according to General Procedure E. The reaction mixture was purified via column chromatography by use of SILICA GEL with n-hexane-acetone (3:1) as eluent.

Yield 6h: 0.510 g (96.3%)
$[\alpha]_D^{25} = -57.37°$ (c=0.19 in CHCl$_3$)
M.p.: 85°–87° C.

Compound 7h was synthesized according to General Procedure F.

Yield 7h: 0.538 g (99.1%)
$[\alpha]_D^{25} = -32.42°$ (c=0.33 in CHCl$_3$)
M.p.: solid oil Compound 9h was synthesized from tripeptide (8) and (S,R,R)-Dolaproinyl-L-Phenylalanineamide-N-(methenyl-2-thiophene) trifluoroacetate (7h) according to General Procedure G. The reaction mixture was purified via column chromatography by use of SILICA GEL with n-hexane-acetone (1:1) as eluent.

Yield 9h: 0.161 g (95.9%)
$[\alpha]_D^{25} = -47.42°$ (c=0.31 in CHCl$_3$)
M.p.: 113°–115° C.

EXAMPLE XIV

Synthesis of L-Dolavalyl-L-Valyl-N-Methyl-(S,S,R)-Dolaisoleucyl-(S,R,R)-Dolaproyl-L-Phenylalaninea-mide-N-(methenyl-2-pyridine) compound (9i)

Compound 4i was synthesized from N-tert-butyloxycarbonyl-L-phenylalanine-N-(methenyl-2-pyridine) (3i) according to General Procedure D.

Yield 4i: 0.576 g (98.7%)
$[\alpha]_D^{25} = +51.44°$ (c=1.04 in CH$_3$OH)
M.p.: 142°–144° C.

Compound 6i was synthesized from Boc-dolaproine (5) and L-Phenylalanine-N-(methenyl-2-pyridine) hydrochloride (4i) according to General Procedure E. The reaction mixture was purified via column chromatography by use of SILICA GEL with n-hexane-acetone (1:1) as eluent.

Yield 6i: 0.487 g (92.9%)
$[\alpha]_D^{25} = -49.22°$ (c=0.51 in CHCl$_3$).
M.p.: 63°–65° C.

Compound 7i was synthesized according to General Procedure F.

Yield 7i: 0.531 g (98.6%)
$[\alpha]_D^{25} = -49.39°$ (c=0.33 in CHCl$_3$)
M.p.: solid oil Compound 9i was synthesized from tripeptide (8) and (S,R,R)-Dolaproinyl-L-Phenylalanineamide-N-(methenyl-2-pyridine) trifluoroacetate (7i) according to General Procedure G. The reaction mixture was purified via column chromatography by use of SILICA GEL with D-hexane-acetone-methanol (8:7:1) as eluent.

Yield 9i: 0.162 g (96.8%)
$[\alpha]_D^{25} = -49.12°$ (c=0.34 in CHCl$_3$)
M.p.: 158°–160° C.

EXAMPLE XV

Synthesis of L-Dolavalyl-L-Valyl-N-Methyl-(S,S,R)-Dolaisoleucyl-(S,R,R)-Dolaproyl-L-Phenylalaninea-mide-N-(1-adamantane) compound (9j)

Compound 4j was synthesized from N-tert-butyloxycarbonyl-L-phenylalanine-N-(1-adamantane) (3j) according to General Procedure D.

Yield 4j: 0.660 g (98.6%)
$[\alpha]_D^{25} = +65.8°$ (c=0.43 in CH$_3$OH)
M.p.: 209°–210° C.

Compound 6j was synthesized from Boc-dolaproine (5) and L-Phenylalanine-N-(1-adamantane) hydrochloride (4j) according to General Procedure E. The reaction mixture was purified via column chromatography by use of SILICA GEL with n-hexane-toluene-isopropanol (6:1:1) as eluent.

Yield 6j: 0.479 g (84.4%)

$[\alpha]_D^{25} = -46.1°$ (c=0.46 in CHCl$_3$).

M.p.: 189°–190° C.

Compound 7j was synthesized according to General Procedure F.

Yield 7j: 0.577 g (99.2%)

$[\alpha]_D^{25} = -30.0°$ (c=0.19 in CH$_3$OH).

M.p.: 125°–126° C.

Compound 9j was synthesized from tripeptide (8) and (S,R,R)-Dolaproinyl-L-Phenylalanineamide-N-(1-adamantane) trifluoroacetate (7j) according to General Procedure G. The reaction mixture was purified via column chromatography by use of SILICA GEL with n-hexane-acetone (2:3) as eluent.

Yield 9j: 0.157 g (89.6%)

$[\alpha]_D^{25} = -54.6°$ (c=0.4 in CHCl$_3$)

M.p.: 133°–134° C.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A compound having the structure:

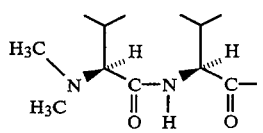

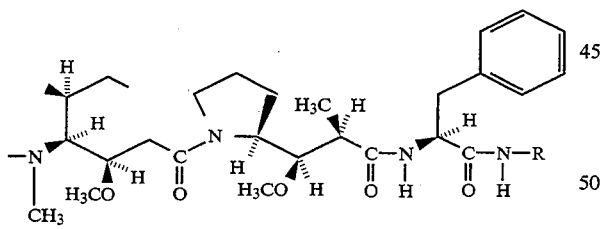

in which R is selected from the group consisting of the substituents designated 9a, 9b, 9c, 9d, 9e, 9g, 9h, 9i, and 9j, as shown below:

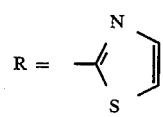
9a

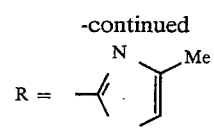
9b

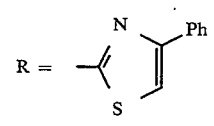
9c

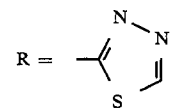
9d

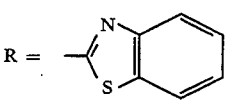
9e

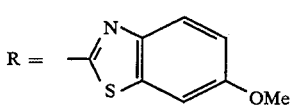
9f

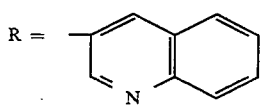
9g

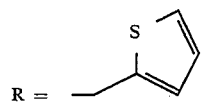
9h

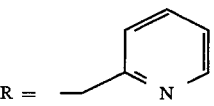
9i

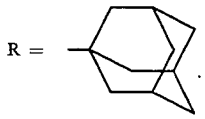
9j

2. A compound according to claim 1 wherein

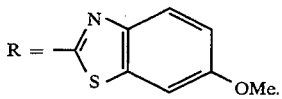

3. A compound according to claim 1 wherein

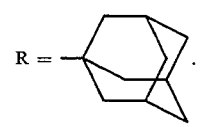

* * * * *